(12) United States Patent
Katou et al.

(10) Patent No.: US 11,119,092 B2
(45) Date of Patent: Sep. 14, 2021

(54) BIOGAS QUALITY EVALUATION DEVICE, BIOGAS QUALITY EVALUATION METHOD, AND PROGRAM

(71) Applicant: MITSUBISHI HEAVY INDUSTRIES, LTD., Tokyo (JP)

(72) Inventors: Yuudai Katou, Tokyo (JP); Yusuke Yamashina, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 0 days.

(21) Appl. No.: 16/971,135

(22) PCT Filed: Feb. 20, 2019

(86) PCT No.: PCT/JP2019/006268
§ 371 (c)(1),
(2) Date: Aug. 19, 2020

(87) PCT Pub. No.: WO2019/167743
PCT Pub. Date: Sep. 6, 2019

(65) Prior Publication Data
US 2020/0378949 A1 Dec. 3, 2020

(30) Foreign Application Priority Data

Feb. 27, 2018 (JP) .............................. JP2018-033365

(51) Int. Cl.
| | | |
|---|---|---|
| G01N 33/497 | (2006.01) | |
| G16B 40/00 | (2019.01) | |
| G06F 17/18 | (2006.01) | |

(52) U.S. Cl.
CPC .......... *G01N 33/497* (2013.01); *G16B 40/00* (2019.02); *G06F 17/18* (2013.01)

(58) Field of Classification Search
None
See application file for complete search history.

(56) References Cited

U.S. PATENT DOCUMENTS

| | | | | |
|---|---|---|---|---|
| 10,101,186 B2 * | 10/2018 | Pretre | .................... | G01N 25/18 |
| 2008/0031809 A1 | 2/2008 | Norbeck et al. | | |

(Continued)

FOREIGN PATENT DOCUMENTS

| | | |
|---|---|---|
| CN | 1396245 | 2/2003 |
| CN | 101169071 | 4/2008 |

(Continued)

OTHER PUBLICATIONS

DE 10354406 A1 translation (Year: 2005).*

(Continued)

*Primary Examiner* — Lina M Cordero
(74) *Attorney, Agent, or Firm* — Wenderoth, Lind & Ponack, L.L.P.

(57) ABSTRACT

In the present invention, an input unit receives input of production conditions relating to a plurality of parameters relating to production of a biogas in a biogas production facility. An index value corresponds to an amount of heat per unit quantity of a biogas generated by the biogas production facility under the production conditions. A condition classifying unit classifies the production conditions on the basis of the plurality of parameters and the index value. An output unit outputs information relating to the result of classification by the condition classifying unit.

7 Claims, 7 Drawing Sheets

(56) References Cited

U.S. PATENT DOCUMENTS

| | | | | |
|---|---|---|---|---|
| 2011/0087470 A1* | 4/2011 | Hames | ............... | G01N 21/359 |
| | | | | 703/2 |
| 2011/0215247 A1* | 9/2011 | Kastner | ............. | G01N 21/3504 |
| | | | | 250/339.07 |
| 2016/0041538 A1* | 2/2016 | Buckenham | .......... | G05B 15/02 |
| | | | | 700/287 |
| 2018/0112142 A1* | 4/2018 | Foody | .................... | G06Q 50/06 |

FOREIGN PATENT DOCUMENTS

| | | | | |
|---|---|---|---|---|
| CN | 103468860 | | 12/2013 | |
| DE | 10354406 A1 * | | 6/2005 | ............ C12M 41/28 |
| JP | 2013-204031 | | 10/2013 | |
| TW | 200815280 | | 4/2008 | |
| WO | 2009/076947 | | 6/2009 | |
| WO | 2014/060423 | | 4/2014 | |

OTHER PUBLICATIONS

International Search Report dated May 14, 2019 in corresponding International (PCT) Patent Application No. PCT/JP2019/006268, with English Translation.

Written Opinion dated May 14, 2019 in corresponding International (PCT) Patent Application No. PCT/JP2019/006268, with English Translation.

"Quality Standards for Wood Chips for Fuel", Japan Woody Bioenergy Association, Feb. 19, 2018, https://www.jwba.or.jp/app/download/11003584392/.

* cited by examiner

BIOGAS QUALITY EVALUATION DEVICE, BIOGAS QUALITY EVALUATION METHOD, AND PROGRAM

TECHNICAL FIELD

The present invention relates to a biogas quality evaluation device, a biogas quality evaluation method, and a program.

Priority is claimed on Japanese Patent Application No. 2018-033365, filed Feb. 27, 2018, the content of which is incorporated herein by reference.

BACKGROUND ART

In recent years, power generation using non-fossil fuels has been required to realize a society capable of sustainable growth. The publication "Quality Standards for Wood Chips for Fuel", [online], Japan Woody Bioenergy Association, [Search on Feb. 19, 2018], Internet <URL: https://www.jwba.or.jp/app/download/11003584392/ 燃料用木質チップの品質規格.pdf> discloses quality standards for wood chips, which are non-fossil fuels.

Biogas power generation is known as a power generation method using a non-fossil fuel. Biogas power generation is power generation in which fuel gas produced by fermentation of bio resources is combusted.

For a single type of bio resource such as a wood chip as in the above-referenced publication, quality evaluation based on dimensions and water content is possible. On the other hand, no proper quality evaluation for biogas has been done. This is because the generated amount of biogas and the energy generated by biogas are changed by the amount and the ratio of various types of bio resources such as food residues, sludge, and excreta and by the state of the gas generation facility, and it is difficult to evaluate the quality of biogas quantitatively.

An object of the present invention is to provide a biogas quality evaluation device, a biogas quality evaluation method, and a program which can appropriately evaluate the quality of biogas.

SUMMARY OF THE INVENTION

According to the first aspect of the present invention, a biogas quality evaluation device includes: an input unit configured to receive input of production conditions relating to a plurality of parameters relating to production of a biogas in a biogas production facility; an index value specifying unit configured to specify an index value that correlates to an amount of heat per unit amount of biogas generated by the biogas production facility under the production conditions; a condition classifying unit configured to classify the production conditions based on the plurality of parameters and the index value; and an output unit configured to output information relating to classification results performed by the condition classifying unit.

According to a second aspect of the present invention, the biogas quality evaluation device according to the first aspect may further include a quality classifying unit configured to classify the production conditions into a plurality of quality classes based on the index value; wherein the condition classifying unit classifies the production conditions based on the plurality of parameters and the quality classes.

According to the third aspect of the present invention, in the biogas quality evaluation device according to the second aspect, the quality classifying unit may be configured to classify the production conditions into a plurality of quality classes based on the index value.

According to a fourth aspect of the present invention, in the biogas quality evaluation device according to any one of the first to third aspects, the output unit may output information indicating a parameter with the highest influence on the index value among the plurality of parameters.

According to a fifth aspect of the present invention, in the biogas quality evaluation device according to any one of the first to fourth aspects, the output unit may output a diagram illustrating a relationship between the plurality of parameters and the index value.

According to a sixth aspect of the present invention, a biogas quality evaluation method includes the steps of: receiving input of production conditions relating to a plurality of parameters relating to production of a biogas in a biogas production facility; specifying an index value that correlates with the amount of heat per unit amount of biogas generated by the biogas production facility under the production conditions; classifying the production conditions based on the plurality of parameters and the index value; and outputting information relating to classified results.

According to the seventh aspect of the present invention, a program which causes a computer to execute: receiving input of production conditions relating to a plurality of parameters relating to production of a biogas in a biogas production facility; specifying an index value that correlates with the amount of heat per unit amount of biogas generated by the biogas production facility under the production conditions; classifying the production conditions based on the plurality of parameters and the index value; and outputting information relating to classified results.

Advantageous Effects of Invention

According to at least one of the above aspects, the biogas quality evaluation device can appropriately evaluate the quality of biogas.

DEFINITION

In the present specification, "specify" means to define a second value that can take a plurality of values using the first value. For example, "specify" means to calculate a second value from the first value, read a second value corresponding to the first value with reference to a table, search for a second value using the first value as a query, and select a second value from a plurality of candidates based on the first value.

First Embodiment

Hereinafter, embodiments will be described in detail with reference to the drawings.

Figure 1:
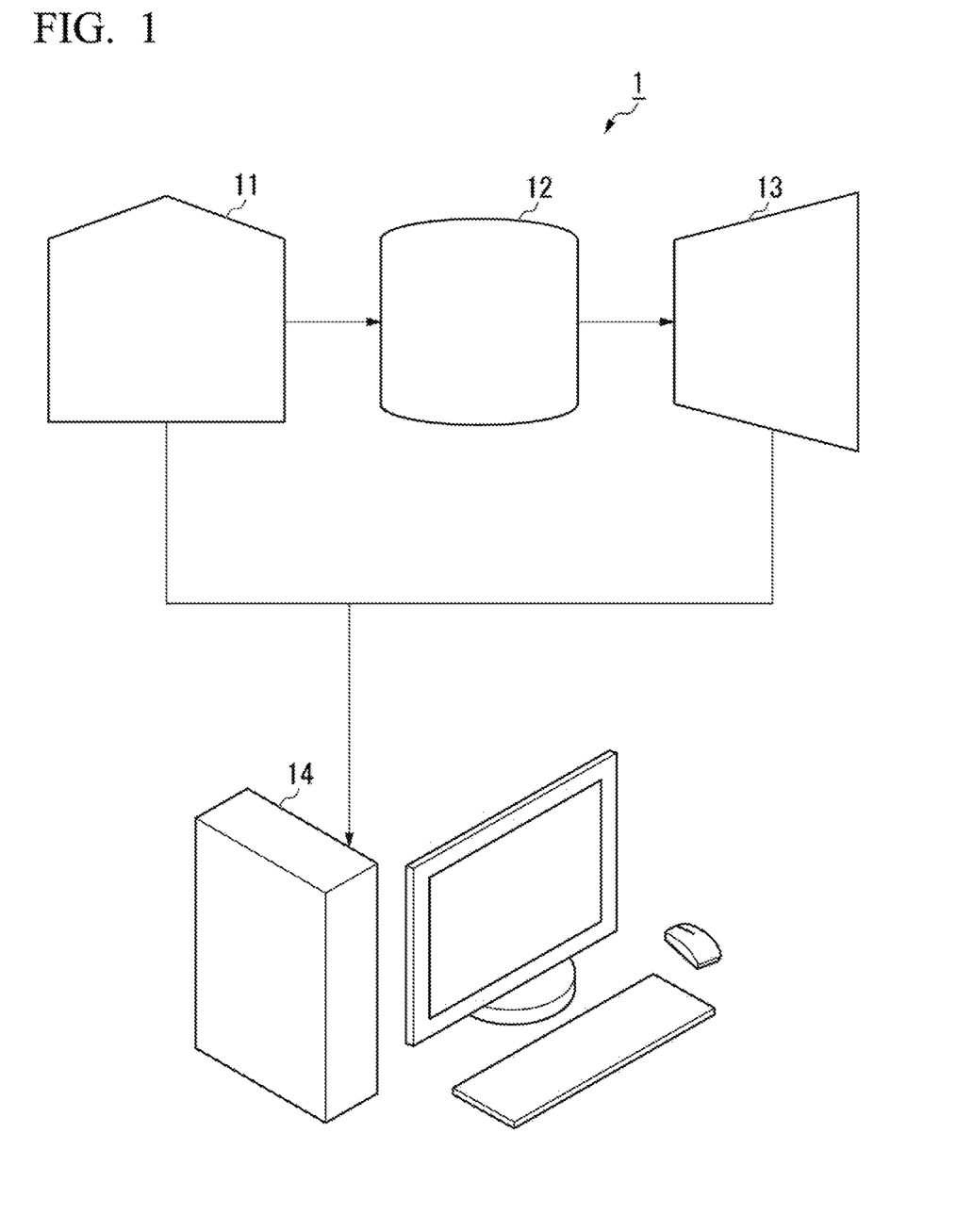
FIG. 1 is a schematic diagram illustrating a configuration of a biogas power generation system according to a first embodiment.

FIG. 1 is a schematic diagram illustrating a configuration of a biogas power generation system according to a first embodiment.

A biogas power generation system 1 includes a fermenter 11, a gas holder 12, a power generator 13, and a biogas quality evaluation device 14.

The fermenter 11 receives inputs of bio resources such as food residues and sludge, and generates biogas through fermentation treatment with methane bacteria. The fermenter 11 is an example of a biogas production facility.

The gas bolder 12 is a tank that holds the biogas generated in the fermenter 11.

The power generator 13 generates electricity by combusting the biogas held by the gas holder 12.

The biogas quality evaluation device 14 specifies information used for evaluating the quality of biogas based on production conditions minting to the production of biogas. The production condition is composed of a plurality of parameters relating to the bio resources, the fermenter 11, and the power generator 13. Examples of parameters constituting the production condition include generated amount of biogas, pH value of the fermenter 11, temperature of the fermenter 11, liquid level of the fermenter 11, input amount of residual removing liquid added to the fermenter 11, type and amount of bio resources input to the fermenter 11, generated energy, and the like.

Configuration of Biogas Quality Evaluation Device

Figure 2:
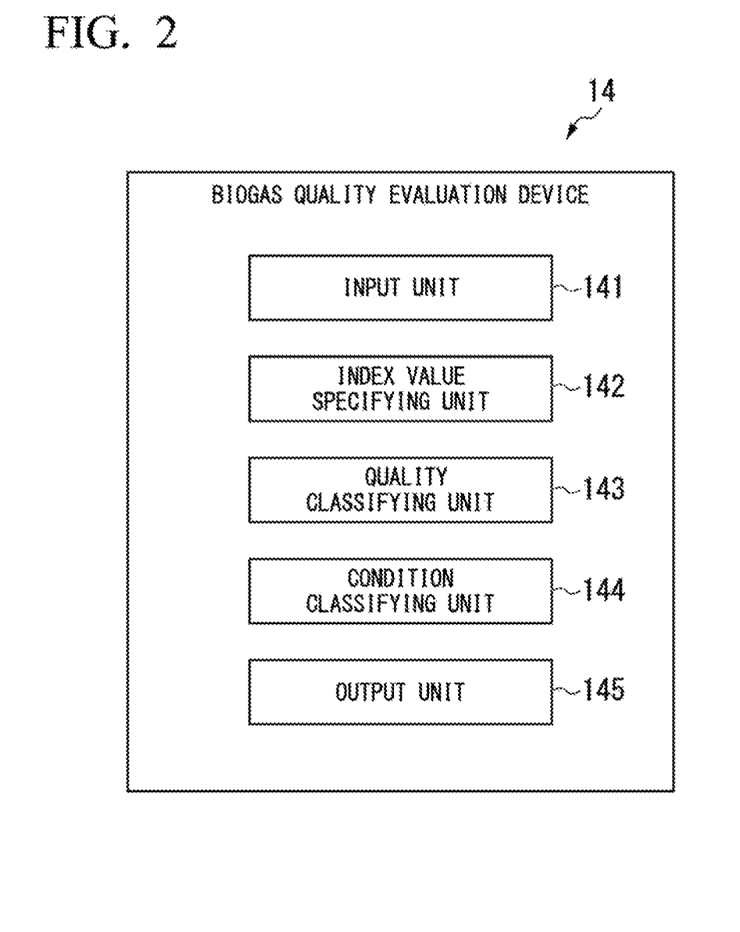
FIG. 2 is a schematic block diagram illustrating a configuration of a biogas quality evaluation device according to the first embodiment.

FIG. 2 is a schematic block diagram illustrating a configuration of a biogas quality evaluation device according to the first embodiment. The biogas quality evaluation device 14 includes an input unit 141, an index value specifying unit 142, a quality classifying unit 143, a condition classifying unit 144, and an output unit 145.

The input unit 141 receives input of production conditions for each biogas production date. The input unit 141 acquires the detection values of the sensors installed in the fermenter 11 and the power generator 13 as the values of the parameters constituting the production conditions, and also receives the input of the values of the parameters from a user. The input unit 141 also receives inputs of the generated amount of biogas and the generated energy by the power generator 13 for each production date.

The index value specifying unit 142 calculates the quality index value of biogas relating to each production date by dividing the energy generated by the power generator 13 input to the input unit 141 for each production date by the generated amount of biogas. That is, the index value specifying unit 142 calculates the quality index value relating to the biogas generated under the production conditions input to the input unit 141. The quality index value is an index value that correlates with the amount of heat per unit amount of biogas. That is, since the generated energy increases as the amount of heat per unit amount of biogas increases and also increases as the generated amount of biogas increases, the index value specifying unit 142 can calculate the quality index value of biogas by dividing the generated energy by the generated amount of biogas.

Figure 3:
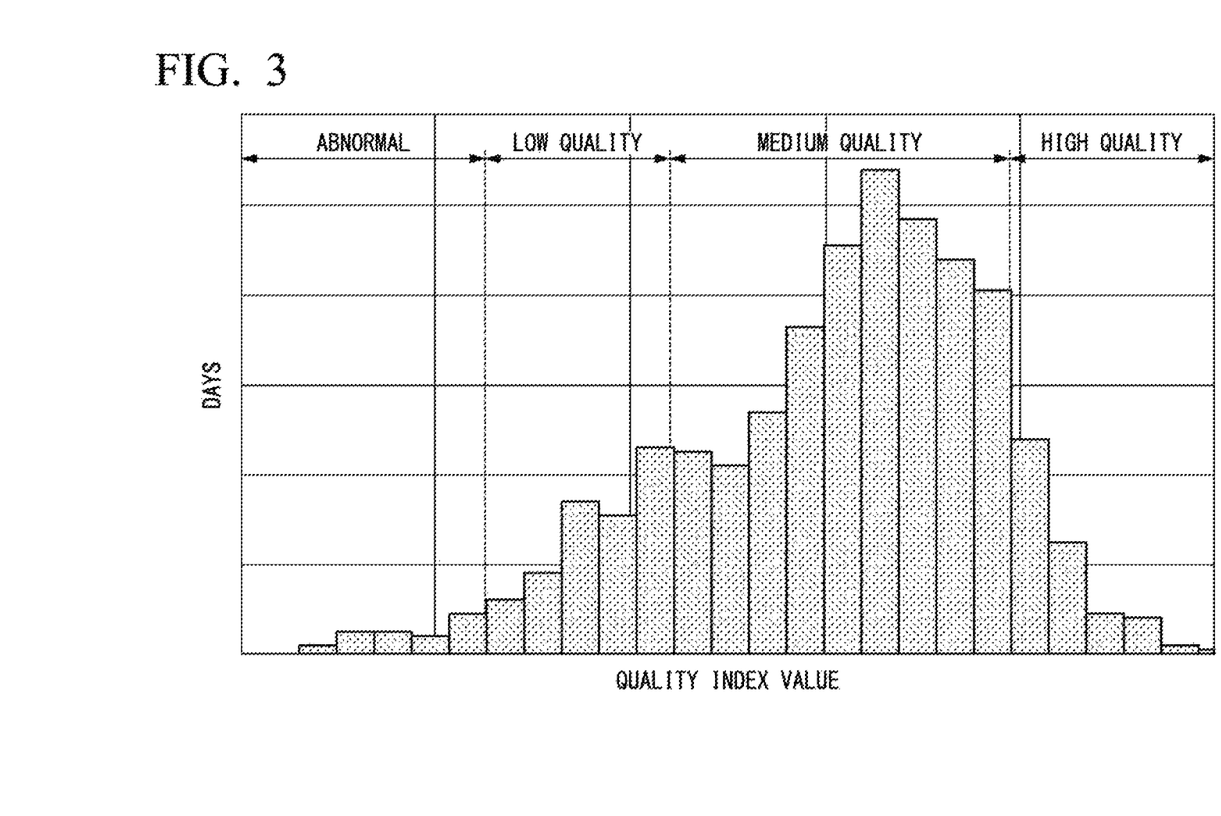
FIG. 3 is a diagram illustrating an example of quality classes according to the first embodiment.

The quality classifying unit 143 classifies the biogas relating to each production date specified by the index value specifying unit 142 into four quality classes (high quality, medium quality, low quality, abnormal) based on the quality index value. FIG. 3 is a diagram illustrating an example of quality classes according to the first embodiment. Specifically, the quality classifying unit 143 classifies the quality of biogas relating to the quality index values belonging to the range of $m+\sigma$ or more into "high quality" based on the average value m and the standard deviation $\sigma$ relating to a plurality of dates calculated by the index value specifying unit 142. The quality classifying unit 143 classifies the quality of biogas relating to the quality index values belonging to the range of $m-\sigma$ or more and less than $m+\sigma$ into "medium quality". The quality classifying unit 143 classifies the quality of biogas relating to the quality index value belonging to the range of the threshold Th or more and less than $m-\sigma$ into "low quality". The quality classifying unit 143 classifies the quality of the biogas relating to the quality index value less than the threshold Th into "abnormal". "Abnormal" in the quality classes is a classification to which biogas whose generated energy is extremely small with respect to the generated amount due to a failure of the generator 13 or the like belongs. The threshold Th may be set manually, or may be determined based on the average value and standard deviation. In addition, the quality classifying unit 143 may classify the quality of biogas into "abnormal" when the generated energy is less than or equal to a predetermined value regardless of the generated amount of biogas. The standard deviation of the quality index value is an example of the variance of the quality index value.

Figure 4:
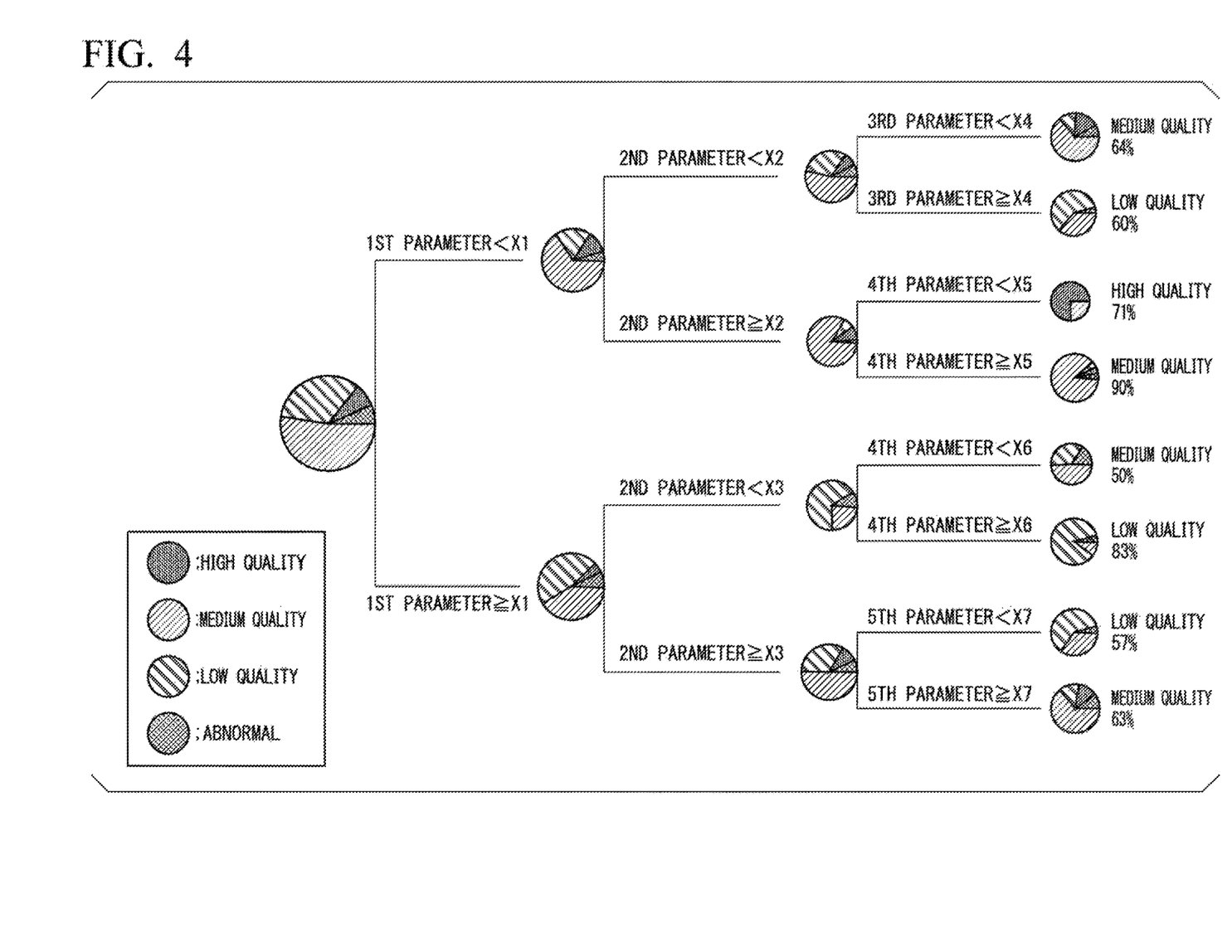
FIG. 4 is a diagram illustrating an example of a decision tree according to the first embodiment.

The condition classifying unit 144 classifies the production conditions input to the input unit 141 based on the quality class classified by the quality classifying unit 143. Specifically, the condition classifying unit 144 generates a decision tree (classification tree) for classifying the production conditions into a plurality of classes based on the production conditions and the quality class. FIG. 4 is a diagram illustrating an example of a decision tree according to the first embodiment. At this time, the condition classifying unit 144 determines the parameters and the threshold values of the production conditions such that the quality class of biogas belonging to the class included in the terminal node of the decision tree is biased (entropy is decreased). The condition classifying unit 144 extends the nodes of the decision tree until the number of elements belonging to the class becomes less than a predetermined threshold value or the entropy of the quality class in the class becomes less than a predetermined threshold value.

The output unit 145 outputs a decision tree generated by the condition classifying unit 144. That is, the biogas quality evaluation device 14 according to the first embodiment outputs a decision tree for specifying the quality class of biogas from the production conditions of biogas. For this reason, the user can specify the quality class of biogas from the production conditions of biogas based on the decision tree. The decision tree is an example of information relating to the classification result.

Operation of Biogas Quality Evaluation Device

Figure 5:
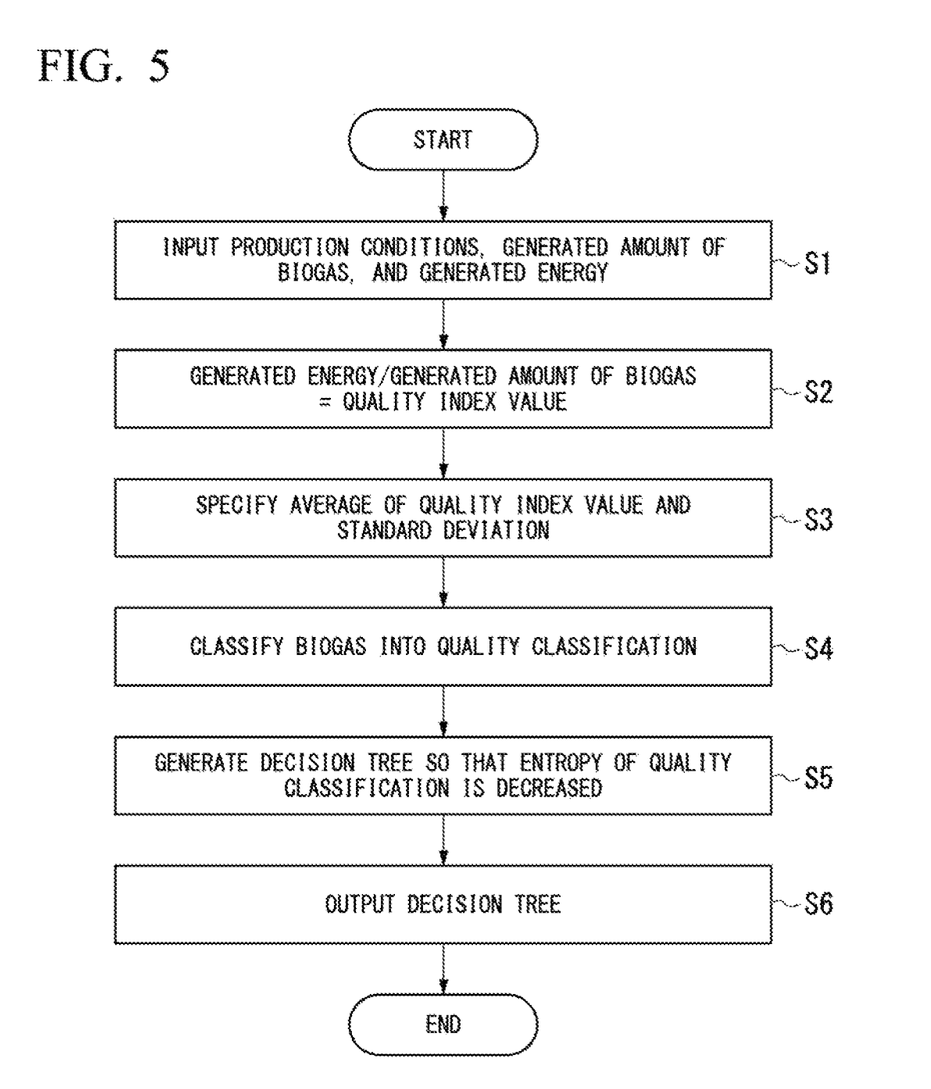
FIG. 5 is a flow chart illustrating an operation of the biogas quality evaluation device according to the first embodiment.

FIG. 5 is a flowchart illustrating operation of the biogas quality evaluation device according to the first embodiment. The input unit 141 receives, from the sensors installed in the fermenter 11 and the power generator 13 and the user, inputs of the values of a plurality of parameters relating to the production conditions of biogas relating to a plurality of production dates, the generated amount of biogas, and the generated energy (step S1). Next, the index value specifying unit 142 calculates the quality index value of biogas relating to each production date by dividing the generated energy of the generator 13 by the generated amount of biogas for each of the plurality of production dates (step S2).

The quality classifying unit 143 obtains the average value m and the standard deviation σ of the plurality of quality index values specified by the index value specifying unit 142 (step S3). The quality classifying unit 143 classifies the biogas relating to each production date into four quality classes based on the quality index value of the biogas relating to the plurality of production dates, the average value m, and the standard deviation σ specified by the index value specifying unit 142 (step S4).

The condition classifying unit 144 generates a decision tree for classifying biogas into a plurality of classes so that the entropy relating to the quality class of the biogas belonging to the class included in the terminal node is decreased based on the quality class classified by the quality classifying unit 143 and the production conditions input (step S5). The output unit 145 outputs the decision tree generated by the condition classifying unit 144 (step S6).

Action and Effect

According to the first embodiment, the biogas quality evaluation device 14 outputs a decision tree that classifies production conditions based on a plurality of parameters relating to the production of biogas in the fermenter 11 and a quality index value that correlates with the amount of heat per unit amount of biogas. For this reason, the user can predict the quality of biogas being produced by checking the current production conditions of biogas in the fermenter 11 against the decision tree. Moreover, the user can recognize the reason why the quality of biogas is low through the decision tree. At this time, since the biogas quality evaluation device 14 generates a decision tree based on the production conditions including the parameters that can be controlled by the user, the user can take measures to improve the quality of biogas. Examples of controllable parameters include pH, temperature, water content, liquid level, input amount of bio resources by type, and the like of fermenter 11. On the other hand, examples of uncontrollable parameters include parameters relating to past gas generation and the like. The decision tree is an example of a diagram illustrating the relationship between a plurality of parameters and quality index values.

Further, according to the first embodiment, the biogas quality evaluation device 14 classifies the production conditions into a plurality of quality classes. For this reason, the biogas quality evaluation device 14 can classify the production conditions through the decision tree by classifying the production conditions so that the entropy relating to the qualify class is decreased. In addition, in another embodiment, the biogas quality evaluation device 14 may not classify the production conditions into a plurality of quality classes. In this case, the biogas quality evaluation device 14 can classify the production conditions by means of a regression tree and the like.

Other Embodiments

Although one embodiment has been described in detail above with reference to the drawings, the specific configuration is not limited to the above, and various design changes and the like are possible.

The biogas quality evaluation device 14 according to the first embodiment outputs a decision tree, but is not limited to this. For example, the biogas quality evaluation device 14 according to another embodiment may output a parameter with the highest influence on the quality index value among the parameters relating to the branch of the decision tree, that is, information indicating the parameter relating to the branch of the root node. For example, in the example shown in FIG. 4, the biogas quality evaluation device 14 may output information indicating that the quality becomes low when the first parameter is X1 or more. Further, the biogas quality evaluation device 14 may output a plurality of higher rank parameters with higher influence on the quality index value. For example, in the example shown in FIG. 4, the biogas quality evaluation device 14 may output information indicating that the quality becomes low when the first parameter is X1 or more and the second parameter is smaller than X3, and information indicating that the quality becomes high when the first parameter is smaller than X1 and the second parameter is X2 or more.

The biogas quality evaluation device 14 according to the first embodiment calculates the quality index value of biogas by dividing the generated energy of the power generator 13 by the generated amount of biogas. On the other hand, the biogas quality evaluation device 14 may use the concentration of biogas as the quality index value. The concentration can be acquired by installing the gas holder 12 with a gas concentration meter. The concentration of biogas is an example of an index value that correlates with the amount of heat per unit amount of biogas.

The biogas quality evaluation device 14 according to the first embodiment displays the generated decision tree, but is not limited to this. For example, the condition classifying unit 144 of the biogas quality evaluation device 14 according to another embodiment may receive an input of the current production conditions of biogas in the fermenter 11 from the user, and specifics the quality class of biogas based on the input, and the output unit 145 may output the specified quality class. For this reason, the user can recognize the quality of biogas being produced. In addition, when the user buys or sells biogas, the price of biogas can be set based on the output quality class.

In addition, the biogas quality evaluation device 14 according to another embodiment may output a plurality of higher rank parameters with higher influence on the quality index value among the parameters used to determine the specified quality class. For this reason, the user can take measures to improve the quality of biogas.

Figure 6:
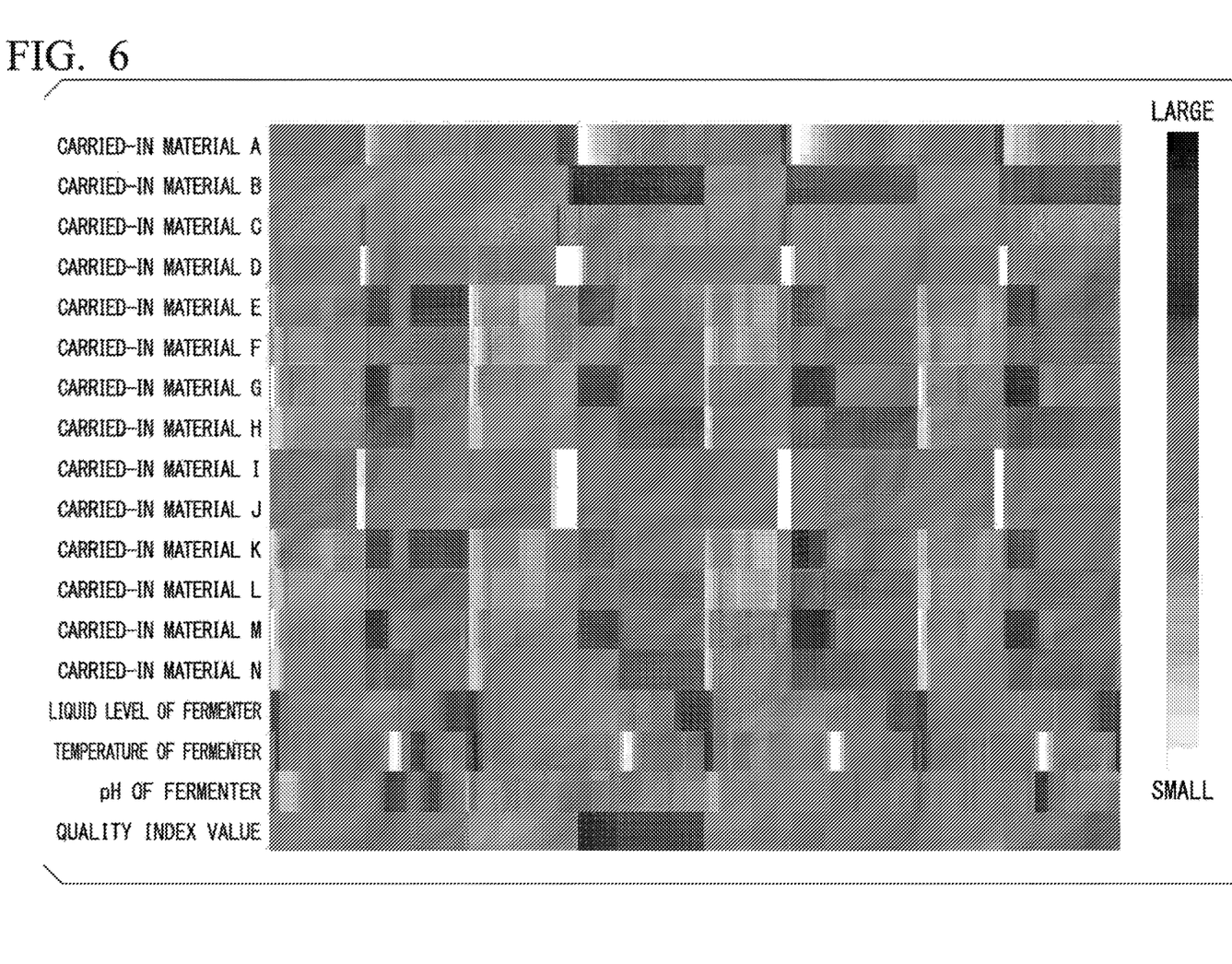
FIG. 6 is a diagram illustrating an example of a heat map.

The biogas quality evaluation device 14 according to the first embodiment classifies production conditions using a decision tree. On the other hand, the biogas quality evaluation device 14 according to another embodiment may classify the production conditions through another method other than the decision tree. For example, the biogas quality evaluation device 14 according to another embodiment may classify the production conditions using another unsupervised learning method such as hierarchical clustering. Specifically, the condition classifying unit 144 of the biogas quality evaluation device 14 clusters the standardized combination of the value of each parameter relating to the production conditions and the quality index value through hierarchical clustering, and generates a diagram showing a heat map by rearranging this by cluster. At this time, the condition classifying unit 144 of the biogas quality evaluation device 14 can prioritize clustering about the quality index value by making a weight of the quality index value higher than another parameter. FIG. 6 is a diagram illustrating an example of a heat map. The heat map shown in FIG. 6 is a graph in which the vertical axis represents the quality index value and each parameter relating to the production conditions and the horizontal axis represents the production date of biogas. As shown in FIG. 6, in the heat map diagram, seeds having similar parameters to each other relating to quality index values and production conditions are arranged in the vicinity. For this reason, the user can specify the parameter condition when the quality is low and the parameter condition when the quality is high. For example, in the example shown in FIG. 6, it can be seen that the quality index value is high when the input amount of the carried-in material B is large. Also, it can be seen that the quality index value is low when the input amount of all the carried-in material is small.

Figure 7:
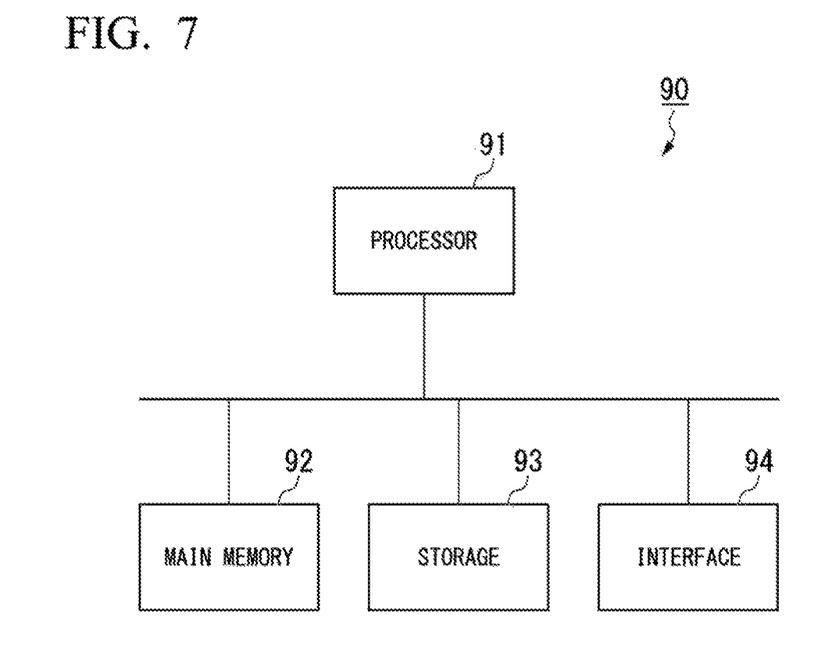
FIG. 7 is a schematic block diagram illustrating a configuration of a computer according to at least one embodiment.

FIG. 7 is a schematic block diagram illustrating a configuration of a computer according to at least one embodiment.

A computer 90 includes a processor 91, a main memory 92, a storage 93, and an interface 94.

The above-described biogas quality evaluation device 14 is mounted on the computer 90. An operation of each of the above-described processing units is stored in the form of a program (algorithm) in the storage 93. The processor 91 reads the program from the storage 93, loads the program on the main memory 92, and performs the process in accordance with the program (algorithm). The processor 91 guarantees a storage region corresponding to each of the above-described storages units in the main memory 92 in accordance with the program.

Examples of the storage 93 are HDD (Hard Disk Drive), SSD (Solid State Drive), magnetic disk, magneto-optical disk, CD-ROM (Compact Disc Read Only Memory), DVD-ROM (Digital Versatile Disc Read Only Memory), Semiconductor memory, and the like. The storage 93 may be an internal medium directly connected to the bus of the computer 90 or an external medium connected to the computer 90 via the interface 94 or a communication line. Further, when this program is distributed to the computer 90 through a communication line, the computer 90 that receives the distribution may expand the program in the main memory 92 and execute the above processing. In at least one embodiment, the storage 93 is a nan-transitory, tangible storage medium.

Further, the program may be a program for realizing some of the functions described above. Furthermore, the program may be a so-called difference file (difference program) that realizes the above-described function in combination with another program already stored in the storage 93.

INDUSTRIAL APPLICABILITY

The biogas quality evaluation device can appropriately evaluate the quality of biogas.

1 Biogas power generation system
11 Fermenter
12 Gas holder
13 Power generator
14 Biogas quality evaluation device
141 Input unit
142 Index value specifying unit
143 Quality Classifying unit
144 Condition classifying unit
145 Output unit

The invention claimed is:

1. A biogas quality evaluation device comprising:
an input unit configured to receive production conditions relating to a plurality of parameters relating to production of a biogas in a biogas production facility;
a processor configured to execute a program to:
specify an index value correlated to an amount of heat per unit amount of the biogas generated by the biogas production facility under the production conditions;
generate a decision tree based on the plurality of parameters and the index value, and determine the plurality of parameters and threshold values of the production conditions such that a quality class of biogas being a class included in a terminal node of the decision tree is biased;
prioritize clustering about the index value by making a weight of the index value higher than other weighting index values of the plurality of parameters; and
generate a diagram based on the index value and the production conditions; and
an output unit configured to output the diagram as information indicating biogas production condition classification results obtained by the processor.

2. The biogas quality evaluation device according to claim 1, wherein the processor is further configured to classify the production conditions into a plurality of quality classes, the index value based on the plurality of parameters and the plurality of quality classes.

3. The biogas quality evaluation device according to claim 2, wherein the processor is further configured to execute the program to classify the production conditions into the plurality of quality classes based on a variance of the index value.

4. The biogas quality evaluation device according to claim 1, wherein the output unit is configured to output information indicating a parameter with highest influence on the index value among the plurality of parameters.

5. The biogas quality evaluation device according to claim 1, wherein the output unit is configured to output a second diagram illustrating a relationship between the plurality of parameters and the index value.

6. A biogas quality evaluation method comprising:
receiving input of production conditions relating to a plurality of parameters relating to production of a biogas in a biogas production facility;
specifying an index value correlated to an amount of heat per unit amount of the biogas generated by the biogas production facility under the production conditions;
generating a decision tree based on the plurality of parameters and the index value, and determining the plurality of parameters and threshold values of the production conditions such that a quality class of biogas being a class included in a terminal node of the decision tree is biased;
prioritizing clustering about the index value by making a weight of the index value higher than other weighting index values of the plurality of parameters;
generating a diagram based on the index value and the production conditions; and
outputting the diagram as information indicating biogas production condition classification results.

7. A non-transitory readable medium comprising a program to be executed by a processor to cause a computer to execute a method, the method comprising:

receiving input of production conditions relating to a plurality of parameters relating to production of a biogas in a biogas production facility;

specifying an index value correlated to an amount of heat per unit amount of the biogas generated by the biogas production facility under the production conditions;

generating a decision tree based on the plurality of parameters and the index value, and determining the plurality of parameters and threshold values of the production conditions such that a quality class of biogas being a class included in a terminal node of the decision tree is biased;

prioritizing clustering about the index value by making a weight of the index value higher than other weighting index values of the plurality of parameters;

generating a diagram based on the index value and the production conditions; and outputting the diagram as information indicating biogas production condition classification results.

* * * * *